(12) United States Patent
Thiriez

(10) Patent No.: US 6,755,623 B2
(45) Date of Patent: Jun. 29, 2004

(54) FLOATING PUMP ASSEMBLY

(76) Inventor: Eric Thiriez, P.O. Box 2923, Cartagena (CO)

(*) Notice: Subject to any disclaimer, the term of this patent is extended or adjusted under 35 U.S.C. 154(b) by 0 days.

(21) Appl. No.: 10/056,997

(22) Filed: Jan. 25, 2002

(65) Prior Publication Data

US 2003/0143082 A1 Jul. 31, 2003

Related U.S. Application Data

(63) Continuation-in-part of application No. 09/923,020, filed on Aug. 6, 2001, now abandoned.

(51) Int. Cl.[7] ............................................. F04B 53/00
(52) U.S. Cl. ........................ 417/61; 417/40; 417/234; 210/219; 210/220; 261/25; 261/93
(58) Field of Search ..................... 417/40, 61, 234, 417/33, 34, 207, 313, 321, 361, 362, 363, 364; 290/53, 54; 210/121, 83, 169, 219, 220, 241, 242.1, 242.2, 242.3, 923; 606/181; 261/25, 29, 91, 92, 93, 120, 242, 121 R; 415/7

(56) References Cited

U.S. PATENT DOCUMENTS

| | | | | |
|---|---|---|---|---|
| 1,920,371 A | * | 8/1933 | Franke | 103/87 |
| 3,496,901 A | * | 2/1970 | Stanfield et al. | 115/12 |
| 3,837,627 A | * | 9/1974 | Sence et al. | 261/29 |
| 3,856,272 A | * | 12/1974 | Ravitts | 259/95 |
| 4,305,894 A | * | 12/1981 | Lindblom | 261/93 |
| 4,526,514 A | * | 7/1985 | Duverne | 417/61 |
| 4,764,053 A | | 8/1988 | Schupbach et al. | |
| 4,807,373 A | | 2/1989 | Sloan et al. | |
| 4,854,058 A | | 8/1989 | Sloan et al. | |
| 5,040,919 A | | 8/1991 | Hendrix | |
| 5,102,308 A | | 4/1992 | Bordelon | |
| 5,297,925 A | | 3/1994 | Lee et al. | |
| 6,113,356 A | | 9/2000 | Eller et al. | |

FOREIGN PATENT DOCUMENTS

DE 3130693 A1 * 6/1982

* cited by examiner

Primary Examiner—Edward K. Look
Assistant Examiner—John Belena
(74) Attorney, Agent, or Firm—Malloy & Malloy, P.A.

(57) ABSTRACT

A floating pump assembly including a compact floatation assembly structured to float on a body of water and supporting a flow pump housing having an inlet, outlet and fluid drive assembly being submerged and wherein at least the outlet is oriented in a predetermined, preferably horizontal orientation during operation and activation. A power assembly is supported on the floatation assembly and is drivingly connected to the fluid drive assembly for powered operation thereof. The predetermined orientation of at least the outlet and particularly the direction of discharge of water issuing from the outlet substantially is such as to eliminate or at least minimize the tendency of the floatation device to become disoriented or unstable at least in terms of being increasingly submerged into a deeper position within the body of water upon activation and operation of the floating pump assembly.

17 Claims, 4 Drawing Sheets

FLOATING PUMP ASSEMBLY

CROSS REFERENCE TO RELATED APPLICATION

The present application is a continuation-in-part application of previously filed, now application having Ser. No. 09/923,020, filed on Aug. 6, 2001 which has been abandoned.

BACKGROUND OF THE INVENTION

1. Field of the Invention

This invention is directed to a floating pump assembly preferably including a high capacity flow pump supported on a floatation assembly in an at least partially submerged location and in a predetermined orientation which substantially eliminates or at least minimizes the tendency of the floatation assembly to become unstable at least in terms of being further submerged into the body of water on which it is floating, during the activation and operation of the pump assembly.

2. Description of the Related Art

The general concept of a floating pump has been known and utilized for a variety of different applications for many years. Such applications include, but are not limited to, drainage, irrigation, transfer pumping, water control at excavation sites, dredging, and others. In use, conventional pumps of the type referred to herein are frequently connected to some type of primary mover or power supply generally including a drive motor. The drive motor is connected in driving relation to a propeller, drive shaft or like mechanism which serves to create a flow of liquid from an inlet location to an outlet location. The transfer of water or any liquid being treated is thereby accomplished as intended.

By way of example only, floating pumps are commonly used in water treatment facilities as down-flow mixers or water aeration devices. As such, the pump housing, including the rotationally driven pump components therein, are typically disposed on some type of floating structure. As in most emergency and industrial applications, the pump housing and accordingly the path of fluid flow created by the operation of the pump are normally vertically oriented. In such a vertical orientation the drive motor or other power generating facility is located above but generally connected to the pump housing so that the power takeoff of the drive motor and the drive elements or working components thereof, are directly connected. Except in situations where the path of fluid flow is directed from an upper level of a body of water down towards the bottom or basin of the body of water, such as in down flow mixtures and certain aeration devices, the path of fluid flow is normally directed in the opposite direction. This is of course typical when floating pumps are used in a drainage application during heavy rain fall or in more common agriculture applications, such as for irrigation and the like.

However, regardless of the specific utilization of the floating pump, the physical structure and location of the power supply, operative components and floatation assembly are such as to typically maintain the pump housing in a vertical orientation. In such a vertical orientation, the power assembly used to drive the operative pump components is secured to the pump housing in a non-submerged location or is otherwise required to be maintained in an enclosed or sealed casing.

Accordingly, upon activation and continued operation known pump assemblies are frequently disoriented by being tilted and/or more deeply submerged in the body of water in which they are floating. Such instability results from the necessity of the floatation assembly to absorb the thrust force of the pump and the weight of the water as it fills the pump interior and the adjacent portions of an associated discharge or delivery conduit. As a result, the dimension and/or configuration of the floatation device or assembly included in many conventionally structured floating pumps must be significantly increased and/or enlarged. Indeed, the disadvantages of conventional floating pumps which include an oversized supporting float structure are significant, and as a result, the specific applications for which such floating pumps may be utilized may be limited.

Obviously, the above is not true in all uses for floating pumps. However, in many situations it is important to maximize the flow capacity of the floating pump, especially when attempting to transfer or otherwise treat large quantities of water. In such situations it would be extremely beneficial to have the ability of a unitized or self-contained floating pump assembly including a pump housing disposed in a predetermined orientation and capable of extremely large flow capacities. Such an improved floating pump assembly could then be driven by a heavy duty power assembly such as, but not limited to, an internal combustion engine. In such a preferred pump assembly, the power assembly could be mounted on a floatation assembly of compact size and dimension and effectively accomplish a forced flow of significantly large quantities of water through an associated, properly oriented pump housing without encountering the instability disadvantages of the type encountered by conventional floating pumps.

Further, in order to overcome many, if not all, of the known problems and disadvantages commonly associated with conventional floating pump assemblies of the general type set forth above, it is preferred that the pump housing, associated drive assembly and resulting path of fluid flow be disposed in the aforementioned predetermined orientation. The preferred predetermined orientation of the pump housing is such as to eliminate the need for an oversized floatation assembly while minimizing the tendency of the pump assembly to submerge deeper into the body of water and below the surface on which the floatation assembly is intended to float. The predetermined orientation of the pump housing, fluid drive assembly and outlet or discharge of the pump housing, would thereby serve to maintain a forced path of water flow through the pump housing. Importantly, the direction of the path of fluid or water flow would eliminate or significantly reduce any reactive thrust force being exerted on the floatation assembly which would cause its instability. Therefore, during the operation of the fluid drive assembly, as well as the transition thereof from a non-operative mode into an operative mode, any tendency of the floatation to be disoriented, such as by being forced into a deeper submerged position would be substantially eliminated or at least significantly reduced.

An improved floating pump assembly of the type generally set forth above, would therefore allow for the utilization of a more compact and manageable floatation assembly dimensioned and otherwise structured to support and maintain a heavy duty power supply, such as the aforementioned internal combustion engine, in an intended floating orientation. However, the size and/or configuration of the floatation assembly of the present invention would not have to be increased or expanded to overcome the tendency of the pump to be re-oriented into a more deeply submerged position in the body of the water, as is common during the start-up and operation of conventional floating pump structures.

SUMMARY OF THE INVENTION

The present invention is directed to a floatation assembly of the type structured to deliver a high capacity fluid flow thereby enabling it to serve as an effective and efficient water treatment or handling facility in a variety of different applications. In addition, the floatation assembly of the present invention is compact as well as being self-contained to the extent of having a pump housing, and the pumping components associated therewith, as well as a power assembly mounted on a single, relatively compact flotation assembly. The flotation assembly can therefore be efficiently transported from one site to another and operatively positioned on the body of water to be treated in a quick and efficient manner.

In a conventional application of a floating pump assembly, the pump housing and power assembly are typically assembled in a single housing or casing and mounted on a floating structure in a generally vertical orientation. As such, the inlet of the pump housing is submerged and the outlet thereof is located above the water surface for appropriate connection to some type of transfer conduit or the like. Therefore, conventional floating pumps of the type described herein are normally oriented such that a reactive or thrust force is exerted on the floatation assembly upon activation of the pump assembly. This reactive force tends to render the floatation assembly unstable including being forced deeper into the body of water. As a result, the size and weight of the floatation structure is frequently enhanced in an attempt to overcome such instability. The capacity of conventional floating pumps are somewhat restricted and many times must only be used in situations where a high capacity fluid flow is not required or expected. Naturally, under certain conditions a plurality of such floating pumps which collectively have the intended capacity to alleviate the emergency or floating conditions, may be required.

Accordingly, the floating pump assembly of the present invention overcomes the well recognized problems and disadvantages associated with conventional floating pump structures. More specifically, the present invention comprises a floatation assembly structured to float on a body of water and including the support platform or like support facility for the mounting of a power assembly thereon. As will be described in greater detail hereinafter, the power assembly is preferably in the form of a high output internal combustion engine, being diesel or gasoline driven, and being of a size and capacity to efficiently power a high capacity fluid drive assembly. The fluid drive assembly is an operative component of the pump and is at least partially mounted within a pump housing. Further, the power assembly is mounted on the support platform of the floatation assembly in either a non-submerged location or within a protected compartment of the floatation assembly which may be disposed below the water surface. In either embodiment, the power assembly is disposed in spaced, driving interconnection to the fluid drive assembly.

As will also be explained in greater detail hereinafter, the floatation assembly comprises, in at least one embodiment, a frame type structure which may include a protective cover, canopy, casing, etc. disposed in a protective position relative to the power assembly. The power assembly is thereby effectively protected from adverse ambient conditions, such as exist during bad weather conditions, even when it is located above deck in a relatively exposed position. Preferably, the protective cover is "convertible" in nature so as to be easily installed in its operative, protective position or removed therefrom as desired.

In at least one preferred embodiment of the present invention the floating pump assembly comprises an axial flow pump defined, at least in part, by the aforementioned fluid drive assembly disposed at least partially on the interior of the pump housing in fluid communication between the inlet and the outlet thereof. However, it is emphasized that the floating pump assembly of the present invention could also incorporate a mixed flow pump, a centrifugal flow pump, a multi-stage flow pump and others.

Accordingly, regardless of the type of pump structure utilized, the recognized disadvantages and problems associated with conventional floating pump assemblies are substantially overcome by orienting the pump housing and/or fluid drive assembly as well as inlet and outlet in a preferred and predetermined operative orientation. In such predetermined orientation, a path of fluid flow is created upon activation and operation of the fluid drive assembly, wherein the path of fluid flow extends through the pump housing from the inlet to the outlet. By way of example, the pump housing, fluid drive assembly and other operative components directly associated with pumping the water along the predetermined path, may define an axial flow pump. However, regardless of the particular pump structure utilized, the path of water flow through the pump housing and/or especially the orientation of the outlet as the water is discharged from the housing, should be such as to negate, minimize or substantially reduce the effect of the reactive or thrust force generated as water fills and is discharged from the pump housing.

Therefore, in its submerged orientation, the flow pump further overcomes the known disadvantages and problems of the type set forth above by being positioned in the aforementioned predetermined orientation. More specifically, the pump housing, fluid drive assembly and particularly the outlet of the flow pump are preferably arranged in a substantially horizontal orientation. As such, both the inlet and outlet of the pump housing are preferably maintained in a submerged position. This serves to establish the aforementioned path of fluid flow through the pump housing in a substantially horizontal direction of travel, dependent on the type of flow pump structure being utilized. Therefore, any reactive force tending to further submerge the floatation assembly or cause its instability, is eliminated or significantly reduced. As a result, there are no significant forces during the initial transfer of the fluid activation assembly from an inactive mode to an active mode or during the continuous operation of the fluid drive assembly which would create the problematic instability of the flotation assembly. The floatation assembly can therefore be of a smaller, more compact dimension and configuration, which of course must be sufficient to support the weight of the power assembly and the structural components of the floatation assembly itself in a floating orientation on the surface of the body of the water.

It is to be emphasized that when utilizing pump structures other than an axial flow pump, the predetermined orientation of the outlet or discharge end of the pump housing should preferably be substantially horizontal. As such, the disposition of other operative components of the flow pump in the aforementioned predetermined orientation could assume positions other than a true horizontal orientation and still serve to minimize the tendency of the floatation assembly to become unstable when the flow pump is operating.

Depending upon the particular practical application to which the floating pump assembly of the present invention is applied, a water transfer conduit may be connected directly to the outlet portion of the pump housing. Such transfer conduit may be of significant length and extend from a point off shore, where the floating pump assembly of the present invention is located, to a water delivery site on or beyond the shore line. In any event, it is to be emphasized that in at least one preferred embodiment of the present invention, both the inlet and the outlet of the pump housing are in a completely or at least partially submerged position. The path of fluid flow created by the operation of the fluid drive assembly and in particular the direction of water flow is oriented so as to minimize any reactive force being exerted on the floatation assembly which would cause its instability. The floatation assembly would not experience any tendency to be physically disoriented or be additionally submerged beyond its normal floating position.

These and other objects, features and advantages of the present invention will become more clear when the drawings as well as the detailed description are taken into consideration.

BRIEF DESCRIPTION OF THE DRAWINGS

For a fuller understanding of the nature of the present invention, reference should be had to the following detailed description taken in connection with the accompanying drawings in which.

Like reference numerals refer to like parts throughout the several views of the drawings.

DETAILED DESCRIPTION OF THE PREFERRED EMBODIMENT

As disclosed in the accompanying drawings, the present invention is directed to a floating pump assembly generally indicated as 10. The floating pump assembly 10 is of the type capable of high capacity fluid flow and particularly adaptable for use on large bodies of water generally indicated as 12 or any other practical application, especially where high capacity liquid flow is required.

Figure 1:
FIG. 1 is a side view showing the floating pump assembly of the present invention in operation.
Figure 2:
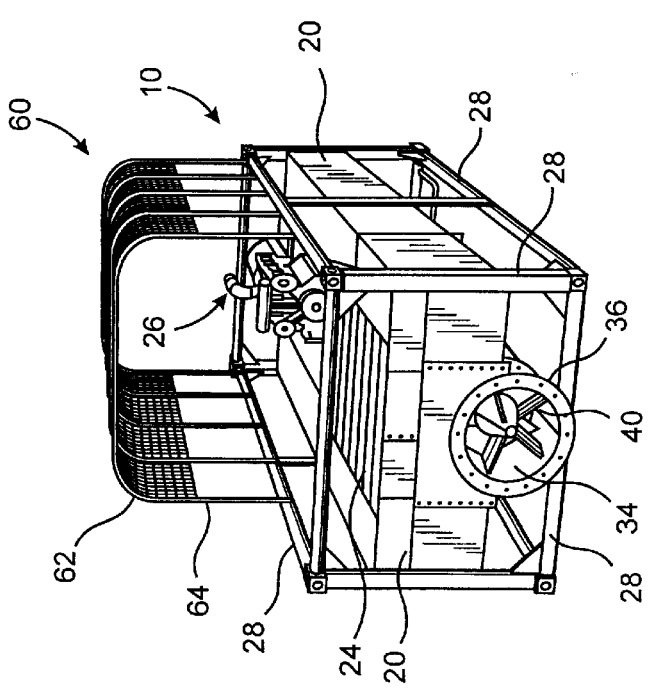
FIG. 2 is a top perspective view of the floating pump assembly of the present invention.

As shown in FIG. 1, the floatation assembly 10 is connected to a transfer conduit schematically represented and generally indicated as 14. The transfer conduit 14 may be of a significant length and extend from the floatation assembly 10 to a point of dispersal, generally indicated as 16. The water being transferred is delivered from the outlet 14' of the transfer conduit 14 into the dispersal area. It is to be noted that the transfer conduit 14 is not per se an included part of the present invention. Of course, it is recognized that the utilization of such a transfer conduit 14, in a variety of different forms may, depending on a specific application, be a necessary part to the successful transfer of water 12, as schematically represented in FIG. 1.

Figure 3:
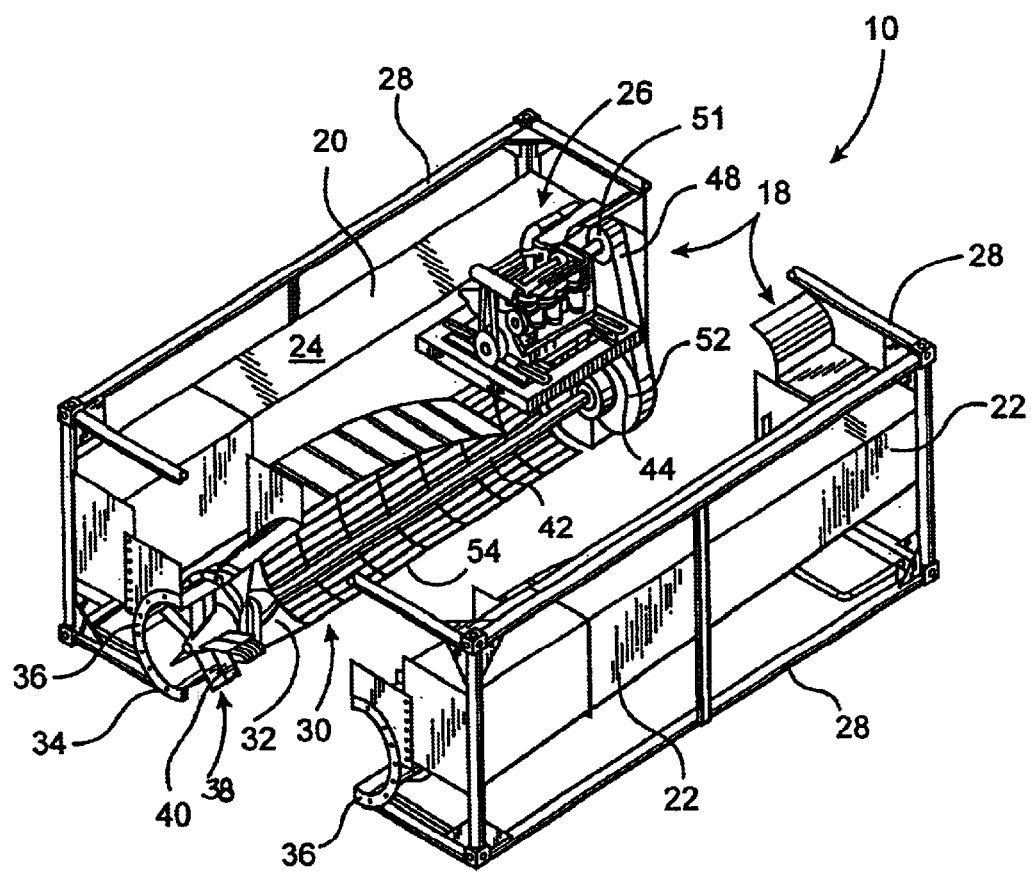
FIG. 3 is a top, at least partially exploded, perspective view of the embodiment of FIGS. 1 and 2.

More specifically, the floating pump assembly 10 of the present invention comprises a floatation assembly generally indicated as 18 and disclosed in FIG. 3 in an exploded form. The floatation assembly 18 includes any applicable floatation structure 20 having a support platform or like supporting facility 22, mounted thereon or being an integral part thereof. As a part of the support platform or like facility 22, a walkway or personnel support 24 may be provided to facilitate access to a power assembly, generally indicated as 26. In the embodiment of FIGS. 1 through 7, the power assembly 26 is disposed in a non-submerged location above the surface 12' of the body of water 12 on which the floatation assembly 18 is operatively positioned.

Other structural features of the floatation assembly 18 include a structural support frame 28 disposed in surrounding, containing relation to the float structure 20, personnel platform 24, power assembly 26 and other operative components of the floating pump assembly 10 to be described in greater detailed hereinafter. Frame 28 may be formed from a metallic or other high strength, relatively light weight material and may be of generally open construction as perhaps best shown in FIGS. 2 and 3.

Another feature of the most preferred embodiment of the present invention comprises the floating pump assembly including a pump housing 30 having an at least partially hollow interior and including a somewhat elongated configuration comprising an inlet 32 and an outlet 34. The outlet 34 is preferably connected to the inlet of the transfer conduit 14 by a flexible coupling 35, as best disclosed in FIGS. 7 and 8. The flexible coupling 35 is structured to accommodate relative movement between the transfer conduit 14 and the flotation assembly 18, such as during rough weather conditions. An annular flange 36 or other connecting structure may be used to establish stable securement of the inlet of the transverse conduit 14 to the outlet 34 of the pump housing 30.

In addition, the present invention comprises a fluid drive assembly generally indicated as 38 and including a pump member 40 preferably in the form of a propeller connected at one end of the elongated drive shaft 42. As will be explained in greater detail with reference to FIG. 7, pump structures other than the axial flow pump may be utilized in the floating pump assembly 10 of the present invention. The opposite end 44 of drive shaft 42 is connected in direct driven relation to the power assembly 26 by a power take-off and drive assembly 46. The power take-off and drive assembly 46 may include any of a variety of different mechanical linkage or gearing assemblies. However, as shown in the preferred embodiment of the present invention, the power take-off assembly 46 includes a drive belt 48 connected between appropriate gears or pulleys 51 and 52, respectively connected to the power take-off of the power assembly 26 and the distal end 44 of the drive shaft 42.

Other features associated with the pump housing 30 include an elongated cage-like structure 54 disposed in at least partially surrounding relation to the drive shaft 42. The cage 54 is formed from an open mesh, apertured or like "flow through" construction which enables the free passage of water therethrough into the inlet 32 of the pump housing 30. The cage prevents engagement and/or interference of any debris or alternatively the bottom of the body of water 12 on which the floating pump assembly 10 is supported, with the fluid drive assembly. Accordingly, the cage 54 extends substantially the entire length of the drive shaft 42 and may or may not be considered a part of the pump housing 30. Appropriate cross braces 56 may be provided so as to supportingly interconnect the cage 54 in its intended, operative position relative to an under portion of the float structure 20 and/or the containment frame 28.

In at least one embodiment of the present invention and as clearly shown in the accompanying Figures, one structural feature of the present invention is the maintenance of the pump housing 30 in a submerged location below the float structure 20, while still being supported in a stable manner on the floatation assembly 18. More specifically, the submerged location of the pump housing 30 is such as to maintain both the inlet 32 and the outlet 34 thereof at least partially submerged and preferably completely submerged during the continuous operation of the fluid drive assembly 38.

Clearly, the propeller 40 is located in fluid communication with both the inlet 32 and the outlet 34. As such, the pump housing 30, inlet and outlet 32 and 34 respectively, drive shaft 42 and other operative components associated with the pump housing 30 and the fluid drive assembly 38 serve to define an axial flow pump. Accordingly, upon rotation of the drive member 40, water will flow through the open construction of the cage 54, into the inlet 32 and coaxially along the length of the pump housing 30. The forced flow of water will be directed outwardly from the outlet 34, in a substantially horizontal direction, into the inlet end of the transfer conduit 14, as described above.

The orientation of the established path of fluid flow, as described above, is therefore substantially coincident with the longitudinal axis of the pump housing 30. In addition, the pump housing 30, fluid drive assembly 38, outlet 34 and resulting path of water flow is disposed in a predetermined orientation which will substantially eliminate or at least minimize any reactive forces being exerted on the floatation assembly 18. Therefore any forces which would tend to destabilize or disorient the floatation assembly 18 or tend to additionally submerge the floatation assembly 18 within the body of water 12, would be substantially eliminated, significantly reduced and therefore minimized. As a result a more effective, compact and efficiently sized and configured float structure 20 and floatation assembly 18 can be used to support the power assembly 26 and pump housing 30 in its intended, operative position. In such operative position the power assembly 26 is of course maintained drivingly interconnected to the drive shaft 42 and pump member 40.

It is emphasized that the aforementioned preferred orientation of the pump housing 30 and in particular the path of water flow as it issues from the outlet 34 is substantially horizontal and in most instances substantially parallel to the median surface level 12'. Therefore, any reactive forces resulting from the activation and continues operation of the fluid drive assembly 40, 42, etc. will not adversely affect the float structure 20 or floatation assembly 18 in a manner which would cause the floatation assembly 18 to become unstable or to be additionally submerged or be drawn deeper below the surface 12' of the body of water 12.

Figure 7:
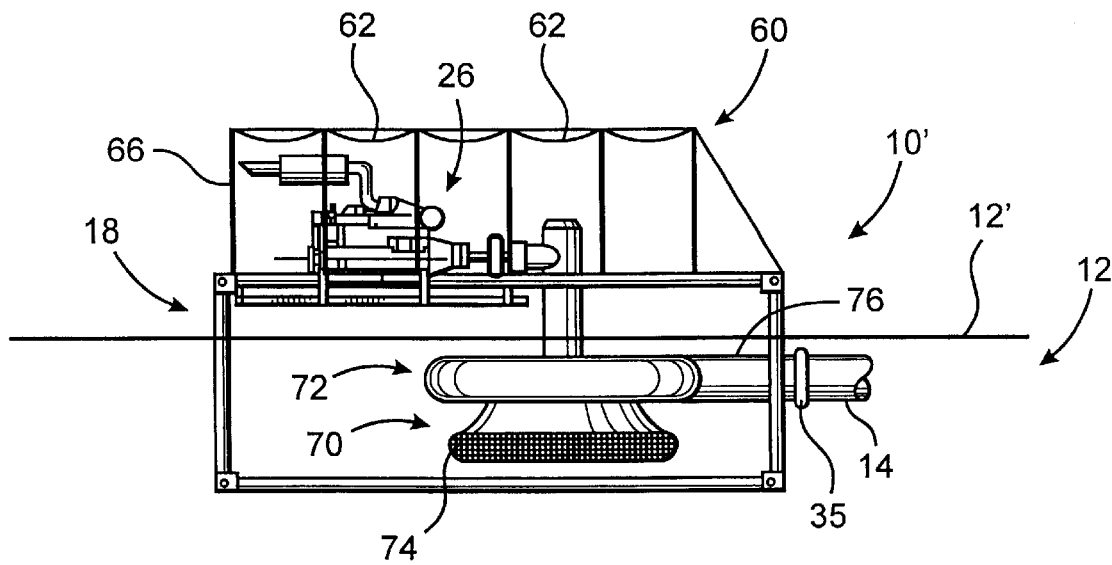
FIG. 7 is a side view of another embodiment of the flotation assembly of the present invention wherein the flow pump utilized is a centrifugal flow pump.

It is further emphasized that when a flow pump other than an axial flow pump is utilized, the aforementioned predetermined orientation of the pump housing, fluid drive assembly, etc. need not assume a true horizontal orientation in order to minimize the aforementioned reactive forces on the flotation assembly 18. For example, as shown in FIG. 7, one preferred embodiment of the floating pump assembly 10' of the present invention includes the utilization of a centrifugal flow pump 70 supported on the floatation assembly 18 in an at least partially submerged position below the water surface 12' of the body of water 12. As such, the centrifugal pump housing 72 includes an inlet 74 and an outlet 76. As set forth above, the outlet 76 is secured to the inlet of the transfer conduit 14 by a flexible coupling 35. Accordingly, while operative components, such as a fluid drive assembly (not shown for purposes of clarity) associated with the centrifugal pump 70 is disposed in a substantially horizontal orientation, the important features of the predetermined orientation of the centrifugal pump 70 is that the outlet 76 is oriented in a substantially horizontal orientation. This predetermined, horizontal orientation of at least the outlet 76 (but preferably other portions of the pump housing 70) serves to eliminate, significantly reduce and thereby minimize any thrust or other reactive forces being exerted on the floatation assembly 18 which would tend to cause its instability. Also, it is emphasized that the axial flow pump of FIGS. 1 through 6 and 8 and the centrifugal flow pump of FIG. 7 are examples only of the various different types of flow pump structures which may be utilized with the floating pump assembly 10, 10' of the present invention. Other pump structures which may be utilized include, but are not limited to, mixed flow pumps, multi-stage pumps, etc. Therefore, the aforementioned predetermined orientation of the path of fluid flow passing through and particularly from the associated pump housing, again dependent on the type of pump structure utilized, while not being truly horizontal, should be other than the normally vertical orientation of many of the floating pump assemblies known and conventionally used.

Figure 5:
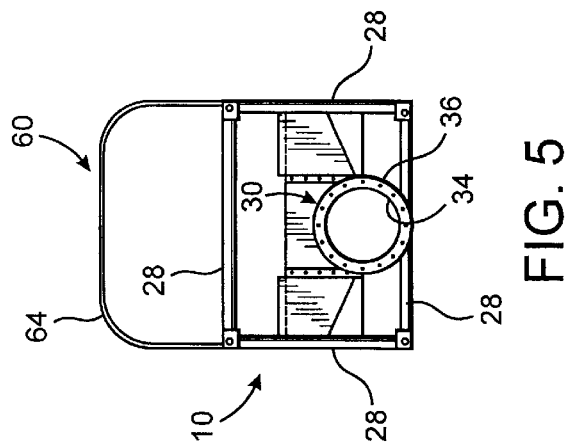
FIG. 5 is an end view of the embodiment of FIG. 4.
Figure 4:
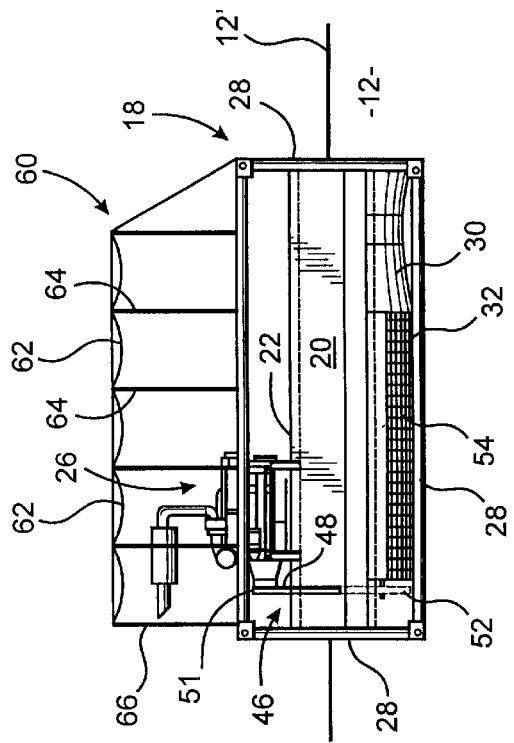
FIG. 4 is a side view of the floating pump assembly of the present invention.
Figure 6:
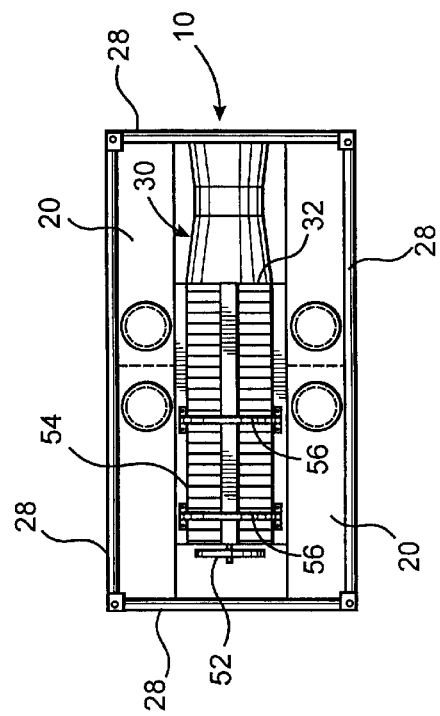
FIG. 6 is a bottom view of the embodiment of FIGS. 4 and 5.

Other structural features of the present invention include a protection assembly generally indicated as 60 and disclosed for use with the embodiments of FIGS. 2 and 4 through 7. The protection assembly 60 preferably comprises a protective cover or the like 62 disposed in overlying, at least partially enclosing and protective relation to the power assembly 26. The power assembly 26 is thereby protected from exposure to adverse ambient conditions such as weather, rough water, etc. The protection assembly 60 may be defined by a variety of different structures having various configurations, sizes, etc. By way of example, and as shown in FIGS. 4 and 5, the protection assembly 60 may be in the form of the cover 62 defined by a flexible material canopy supported by spaced apart substantially arcuate type braces 64 including an opening or vent area 66 to accommodate the exhaust gasses from the power assembly 26.

Figure 8:
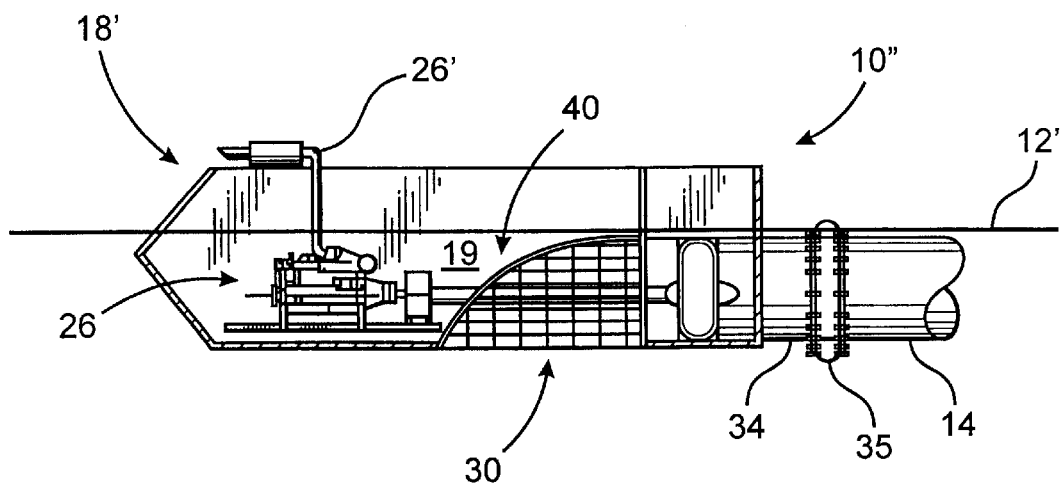
FIG. 8 is a side view of yet another preferred embodiment of the flotation assembly of the present invention wherein a power assembly associated therewith is located on an interior of a flotation assembly at a below deck location.

Yet another preferred embodiment of the present invention is disclosed in FIG. 8 wherein the floating pump assembly 10" includes the floatation assembly 18' having a hull-like configuration defining an open area or chamber 19 located below deck and/or at least partially below the surface 12' of the body of water 12. The power assembly 26 is located within the below deck chamber 19 and is thereby contained in a location which is substantially protected from exposure to unfavorable ambient conditions, such as harsh weather, wind, etc. which would tend to expose the power assembly 26 to waves, water, rain, etc. Accordingly, while the power assembly 26 is located below deck, within the chamber 19 it is of course not "submerged" in the true sense. Exhaust facility such as at 26' are provided to extent upwardly from the chamber 19 so as to vent the exhaust to atmosphere. Naturally, the power assembly 26 is maintained in driving relation to the fluid drive assembly generally indicated as 40. For purposes of example only, the type of pump structure utilized is the axial flow pump as should be evident.

Accordingly, the floating pump assembly of the present invention overcomes many of the disadvantages and problems recognized in this area of commerce by providing a flow pump which is oriented so as to define a path of forced fluid flow being discharged from an outlet in a predetermined, at least substantially horizontal direction. The predetermined orientation of the water discharge outlet in this manner thereby eliminates or at least minimizes any thrust or reactive force being exerted on the floatation assembly 18, which would tend to physically disorient or destabilize it during operation or activation thereof as the flow pump changes from an inactive mode to an active mode.

Since many modifications, variations and changes in detail can be made to the described preferred embodiment of the invention, it is intended that all matters in the foregoing description and shown in the accompanying drawings be interpreted as illustrative and not in a limiting sense. Thus, the scope of the invention should be determined by the appended claims and their legal equivalents.

Now that the invention has been described,

What is claimed is:

1. A floating pump assembly comprising: a) a flotation assembly structured to float on a body of water, b) a pump housing including an inlet and an outlet and a fluid drive assembly disposed in fluid communication with said inlet and said outlet comprising an elongated drive shaft, said pump housing is mounted on said flotation assembly so as to be at least partially filled and submerged in water between said inlet and said outlet, and said pump housing and said fluid drive assembly are collectively oriented to at least partially define an axial flow pump, c) said fluid drive assembly structured to establish a path of fluid flow between said inlet and said outlet and being at least partially disposed coincident to a longitudinal axis of said pump housing, d) said pump housing supported on said flotation assembly and disposed to orient at least said outlet in a predetermined orientation which minimizes physical disorientation of said flotation assembly, e) said inlet and said outlet disposed in a submerged position during operative and inoperative periods of said fluid drive assembly, and a cage structure including a substantially open construction and disposed in spaced at least partially surrounding relation to said drive shaft.

2. A floating pump assembly as recited in claim 1 wherein said fluid drive assembly is at least partially mounted within said housing and is at least partially submerged during activation thereof.

3. A floating pump assembly as recited in claim 2 wherein said pump housing is disposed in a predetermined orientation relative to the surface of the body of water so as to facilitate increased stability of said flotation assembly operation of said fluid drive assembly.

4. A floating pump assembly as recited in claim 3 wherein said predetermined orientation is such as to minimize increased submersion of said flotation assembly during transition of said fluid drive assembly from an inoperative mode to an operative mode.

5. A floating pump assembly as recited in claim 1 wherein said pump housing and said outlet is disposed in a predetermined orientation which reduces submersion of said flotation assembly during operation of said fluid drive assembly.

6. A floating pump assembly as recited in claim 5 wherein said predetermined orientation further reduces submersion of said flotation assembly during transition of said fluid drive assembly from an inoperative mode to an operative mode.

7. A floating pump assembly as recited in claim 6 wherein said predetermined orientation is at least partially defined by said inlet, said outlet and said fluid drive assembly disposed beneath the surface of the body of water in a substantially common predetermined orientation.

8. A floating pump assembly as recited in claim 7 wherein said common predetermined orientation is at least partially defined by a substantially horizontal orientation.

9. A floating pump assembly as recited in claim 1 wherein said predetermined orientation is at least partially defined by a substantially horizontal orientation of said outlet.

10. A floating pump assembly as recited in claim 1 further comprising a power assembly mounted on said flotation assembly in spaced relation to said pump housing and connected in driving relation to said fluid drive assembly.

11. A floating pump assembly comprising: a) a flotation assembly structured to float on a body of water and including a pump housing supported thereon, b) said pump housing having an inlet and an outlet and a fluid drive assembly disposed in fluid communication therewith, c) a power assembly supported on said floatation assembly in connected, driving relation to said fluid drive assembly, d) said inlet, said outlet and said fluid drive assembly being at least partially submerged and at least said outlet disposed in a predetermined orientation which facilitates stabilization of said flotation assembly upon activation and operation of said fluid drive assembly, e) said fluid drive assembly comprising a drive member mounted within said pump housing and disposed and structured to establish a path of fluid flow from said inlet to said outlet upon operation of said fluid drive assembly, f) said fluid drive assembly further comprising an elongated drive shaft connected to said drive member and rotatable therewith, said drive shaft rotationally connected to and driven by said power assembly, and g) said drive shaft extending outwardly from said pump housing along a length of said flotation device and a cage structure including a substantially open construction and disposed in spaced at least partially surrounding relation to said drive shaft.

12. A floating pump assembly as recited in claim 11 further comprising a protection assembly mounted on said flotation assembly in at least partially enclosing relation to said power assembly and structured to protect said power assembly against exposure to adverse ambient conditions.

13. A floating pump assembly as recited in claim 11 wherein said predetermined orientation and said path of fluid flow are substantially horizontally disposed.

14. A floating pump assembly as recited in claim 11 wherein said cage extends along at least a majority of said drive shaft.

15. A floating pump assembly as recited in claim 11 wherein said inlet, said outlet and said fluid drive assembly are structured to collectively comprise a centrifugal flow pump wherein said predetermined orientation of said outlet is substantially horizontal.

16. A floating pump assembly as recited in claim 11 wherein said inlet, said outlet and said fluid drive assembly are disposed in a substantially horizontal orientation.

17. A floating pump assembly as recited in claim 16 wherein said inlet, said outlet, said fluid drive assembly and said pump housing collectively define an axial flow pump.

\* \* \* \* \*